United States Patent [19]

Gabarro

[11] Patent Number: 4,975,373

[45] Date of Patent: Dec. 4, 1990

[54] PROCESS FOR THE PREPARATION OF SULPHUR-CONTAINING HYDROCARBON CHAINS

[75] Inventor: Alberto B. Gabarro, Madrid, Spain

[73] Assignee: Megara Iberica S.A., Spain

[21] Appl. No.: 509,851

[22] Filed: Apr. 17, 1990

Related U.S. Application Data

[62] Division of Ser. No. 265,573, Nov. 1, 1988.

[30] Foreign Application Priority Data

Nov. 2, 1987 [ES] Spain .................................. 8703120

[51] Int. Cl.$^5$ ........................ C12P 5/00; C12N 1/20; C07H 1/00
[52] U.S. Cl. .............................. 435/166; 435/252.4; 435/252.9; 435/253.4; 435/252.1; 435/853; 435/822; 435/882; 435/253.6; 435/262; 435/909; 536/1.1; 536/18.5; 536/45; 536/124; 536/127
[58] Field of Search .................. 435/166, 252.4, 252.9, 435/253.4, 252.1, 853, 822, 882, 253.6, 262, 909; 428/DIG. 17; 536/1.1, 45, 18.5, 124, 127

[56] References Cited

U.S. PATENT DOCUMENTS

| 4,124,501 | 11/1978 | Yen et al. | 435/262 |
| 4,242,448 | 12/1980 | Brown | 435/168 |
| 4,584,271 | 4/1986 | Stern et al. | 435/167 |

*Primary Examiner*—Ronald W. Griffin
*Assistant Examiner*—Pamela Webber
*Attorney, Agent, or Firm*—Steinberg & Raskin

[57] ABSTRACT

Process for the preparation of sulphur-containing hydrocarbon chains, which consists in producing a fermentative action of two types of bacteria, lactic bacteria and bacteria of the genus Desulfovibrio, in a medium of soluble carbohydrates, to which culture medium sulphur is added in the form of salts or as elemental sulphur, the fermentation process being stopped at the point at which the proportion of sulphur-containing carbohydrate reaches its maximum, by means of alkalinization of the medium and subjecting the latter to a thermal shock at between 80° and 90° C., the medium finally being acidified or neutralized.

As a variant, sulphur is bound directly to carbohydrate molecules with a reaction time inversely proportional to the working pressures and temperatures.

3 Claims, No Drawings

PROCESS FOR THE PREPARATION OF SULPHUR-CONTAINING HYDROCARBON CHAINS

This is a division, of application Ser. No. 265,573, filed Nov. 1, 1988.

BACKGROUND OF THE INVENTION

In nature, a series of microbial processes of degradation of organic matter occur, in some cases via pathways different from aerobic oxidative combustion or from anaerobic digestion, in which processes different microbes which act symbiotically generally participate. Advantage may be taken of some of these natural processes, appropriately directed, in order to obtain new products by fermentative biological means.

Among these symbiotic processes, there is one in which two types of bacteria mainly participate, the bacteria in question being lactic bacteria, such as lactobacilli and streptococci, which produce lactic acid from hydrocarbon chains, as in carbohydrates, and other bacteria, of the genus Desulfovibrio, which use the lactic acid produced by the above bacteria as a primary energy source, and the anionic sulphur groups-which, in this biological process, bind to the carbohydrates-as a secondary energy source. Thus, in one phase of the process, sulphur-containing hydrocarbon chains are produced. Specifically, while on the one hand the Desulfovibrio profit from the lactic acid produced by the lactic bacteria, the latter in turn profit from a series of biotic components which stimulate their growth and metabolism, the most important of these being specifically these sulphur-containing carbohydrates, which represent potent activators of lactic bacteria, likewise acting to stabilize and protect these bacteria from oxidizing products, peroxides, and the like, which are produced in the process.

The subject of this patent is hence the use of this natural process for the production of these compounds which activate lactic fermentation, sulphur-containing carbohydrates, but with a careful adjustment of its working conditions in order to direct this fermentation optimally towards the production of these compounds in an acceptable yield.

It is extremely well known that lactic bacteria, mainly lactobacilli and streptococci, in addition to participating in many natural processes, have been used for thousands of years for obtaining fermented foods, including milk products, sausages, pickles and olives, apart from the production of lactic acid, so that no special explanation regarding them is required.

On the other hand, bacteria of the genus Desulfovibrio, of which the most important species is the species Desulfovibrio desulfuricans, are little known despite their abundance, and were discovered by Beijerinck who, in 1885, described their metabolism and properties. The most important subsequent publication was that of Baars, J. K., in 1930, over Sulfataat reductie door Bacterien. W. D. Meinema, N. V. Delft, Holland, nothing important having been published about them since then. They are saprophytic bacteria which are found in abundance in decomposing topsoils, humus, sewage and seafloor sludges. They are completely harmless bacteria for man and animals, in whose bodies the substrate and conditions which they require are impossible to find. They are very ancient bacteria which have evolved very little, that is to say they are stable from the genetic standpoint, which makes them resistant to possible mutations which might give rise to anomalous processes. For this process, special strains have been isolated, which have confirmed the regularity and constancy of their characters over numerous generations, so there are no problems of degeneration with time, as occurs with other bacteria, including lactic bacteria. Specifically, an important action of Desulfovibrio is to protect lactic bacteria from their degradation, attack by phage and mutations.

The novelty of this invention is specifically the use of fermentative biological means for obtaining this type of compound, since reactions employing chemical means (synthesis) which can produce them have been known since the last century. The vulcanization of rubber, discovered by Goodyear in 1839, by inserting sulphur atoms in the hydrocarbon chains of rubber, was the first. Subsequently, in the solubilization of cellulose for obtaining rayon, other processes using carbon disulphide to supply sulphur to the cellulose were invented. Many reactions of this kind are to be found in the literature of the beginning of the present century. The biological means used in this invention represents a natural process, within an ecological order.

DESCRIPTION OF THE INVENTION

The basis of the process which is the subject of the invention consists essentially in producing a fermentative action of these two types of bacteria, lactic and Desulfovibrio, which act symbiotically, in a culture medium with soluble carbohydrates which provide the hydrocarbon chains, mainly disaccharides such as sucrose or lactose, or monosaccharides such as glucose, or mixtures of polysaccharides obtained by means of hydrolysis of starches, and the like, which are normally utilizable by lactic bacteria producing lactic acid.

The fermentation in question is advantageously carried out at temperatures between 30° and 45° C., at a pH between 6.0 and 4.0, preferably using lactic bacteria that produce lactic acid in the (+)-L-lactic isomeric form.

To this culture medium, sulphur is added as sodium, potassium or ammonium sulphate, sulphite, thiosulphate or sulphide salts, or mixtures thereof, and including elemental sulphur (flowers of sulphur), and the like. Calcium sulphate, being only sparingly soluble, is less well metabolized; nevertheless, in the natural process, it is the compound found in the largest amount. The Desulfovibrio bacteria reduce this sulphur, when present in the oxidized state, which binds to the carbohydrates via their most reactive group. Already reduced forms of sulphur can obviously not be reduced, or can only be reduced to a small extent, but appear to act as catalysts or activators of the reaction.

According to the invention, it proves essential to stop the process at the precise point at which the proportion of sulphur-containing carbohydrate reaches its maximum since, if the fermentation continues, it becomes degraded and its content falls. This stopping of the reaction is achieved by alkalinizing the medium to a pH between 8 and 10, and subjecting it to a thermal shock, at between 80° and 90° C., whereby, apart from pasteurizing the medium, removing the bacteria and inactivating the enzyme systems responsible for these reactions, the sulphur-carbohydrate binding is fixed. Subsequently, the medium is acidified or neutralized to a pH between 3 and 6, the final pH depending on whether it is intended to obtain a stable liquid concentrate or to proceed to its immediate dehydration.

For this process, it is not necessary to use pure carbohydrates, but industrial byproducts containing a high proportion of them. To this end, sugar molasses, enzymatic hydrolysates of flours or starches and wheys, and other milk byproducts bereft of proteins, are fully suited to the abovementioned process. These impure substrates similarly provide biotic factors which promote the fermentation.

Neither is it essential to work under sterile conditions, since an intensive pasteurization of the medium at 90° C. suffices to remove all microorganisms which might cause interference. Similarly, since both the lactic flora and the Desulfovibrio bacteria are microorganisms which withstand high osmotic pressures, a simple rise in the latter, by means of the addition of electrolytes such as sodium or potassium chloride (in instances where the osmotic pressure due to the sulphates or carbohydrates is not sufficient) is enough to inhibit the possible growth of other microorganisms without affecting those which are desired.

As an anticipated variant which it is possible to cary out, the incorporation of sulphur into hydrocarbon chains may be achieved directly, by chemical means, by combining the sulphur originating from elemental sulphur, from sulphides or from hydrogen sulphide gas, or from mixtures thereof, with carbohydrate molecules in a purified state and under precise conditions of temperature, pressure, pH and time and in the presence of appropriate catalysts.

To this end, it is necessary to use purer carbohydrate substrates, which may be glucose or dextrose, sucrose, lactose, maltose, sugars originating from hydrolysed starches, deproteinized, demineralized and rectified dairy wheys, rectified and purified sucrose molasses, and the like, combining them with active sulphur originating from soluble sulphides such as sodium or potassium sulphide, and the like, or from insoluble sulphides such as iron sulphide, by acid treatment, or from elemental sulphur, or from mixtures thereof, working at temperatures between 80° and 140° C. with pressures between 0 and 5 kg per cm$^2$, for times inversely proportional to these temperatures and pressures. The reaction medium is adjusted to a pH between 4.0 and 10.0 according to its phase, by acidification with sulphuric or hydrochloric acid, and the like, or alkalinization with sodium, potassium, ammonium or calcium hydroxide, or corresponding mixtures thereof.

An example of embodiment which will facilitate the understanding of the scope of the invention is described below:

EXAMPLE

The inocula or "starters" of the bacteria used in the process are separately prepared beforehand, the bacteria in question being Lactobacillus plantarum or another species, in a suitable medium of molasses and traditional biotic factors such as yeast extract, and the like, and Desulfovibrio desulfuricans, also in a medium of molasses, maize solubles (or corn steep) and sodium lactate and sulphate. The preparation is carried out in fermenters of 50 liters capacity and under sterile conditions.

The suspension is kept pH-stated at between 5.0 and 6.0 with the automatic measured addition of dilute sodium hydroxide or carbonate, and at a temperature of 37° C., with intermittent and very gentle agitation.

When a cell concentration of the order of $10^8$ per milliliter is obtained, the suspension is poured into an industrial fermenter containing 10,000 liters of industrial culture medium consisting of sugar molasses diluted to a concentration of 20% of solids, and, optionally, maize maceration solubles (corn steep) in a proportion of 0.2 to 1%. To this broth, 2% of sodium chloride and 2% of sodium sulphate, as a supply of sulphur, are added. This broth should be pasteurized at a minimum of 80° C. for 20 seconds, in order to destroy undesirable bacteria present in vegetative form. A total sterilization of the medium in order to remove sporulated forms is not essential, since the high osmotic pressure of the medium, with the slightly low pH, inhibits their growth, whereas both the lactobacilli and the Desulfovibrio bacteria tolerate this high osmotic pressure well.

The suspension is kept pH-stated at between 5.0 and 6.0 by means of the automatic measured addition of alkali (sodium hydroxide or carbonate) which, with the lactic acid produced by the lacto bacilli, forms sodium lactate, which the Desulfovibrio bacteria utilize as an energy source, these bacteria, furthermore, reducing the sulphur, which binds to the sucrose molecules. The temperature is maintained at 37° C., cooling being essential when the fermentation is active since heat is generated. The broth is agitated very slowly and intermittently in order to avoid the dissolution of oxygen, which would have an unfavourable effect on the fermentation, which is strictly anaerobic.

When the sulphur content incorporated in the sucrose molecules reaches a maximum, this being determined analytically and normally occurring between 48 and 72 hours after the start of fermentation, the culture is alkalinized with sodium or calcium hydroxide, or a mixture of the two, to pH 8.0–10.0, and heated to between 80° and 90° C. for between 8 and 1 minutes, these factors being linked: the higher the temperature, the shorter the time. Under these conditions, the bacteria disappear and their bodies are even lysed, and the sulphur remains fixed in the sucrose. The mixture is subsequently cooled and neutralized with hydrochloric acid, even adding excess acid, to leave it at a pH between 6.0 and 3.0.

This results in a broth containing approximately 24% of dry matter, about 2,600 kg in the 10,000 liters (equivalent to 11,000 kg), of solids rich in sulphur-containing sucrose with 1% of sulphur in these solids. The remainder of the sulphur which is not incorporated remains as sodium sulphate, or is removed as a calcium sulphate precipitate if calcium hydroxide is used as alkalinizing agent.

A liquid having a not unpleasant aromatic smell remains, and the concentration of this liquid must be completed by vacuum evaporation. This concentrate, containing 60% of dry matter and having a pH of 3.0, keeps well for several months. At a higher pH, 6.0, it is essential to dehydrate it in order to preserve it but, since it is impossible to dehydrate it alone due to its very hygroscopic nature, it should be mixed with other agents that facilitate drying, using a spray-drying tower or other procedures: vacuum pans, and the like.

I claim:

1. Process for the preparation of sulphur-containing hydrocarbon chains, which consist essentially in producing a fermentative action of two types of bacteria, lactic bacteria and bacteria of the genus Desulfovibrio, in a culture medium with soluble carbohydrates, the said fermentation being carried out at temperatures between 30° and 45° C. and at a pH between 6.0 and 4.0, to which culture medium sulphur is added in the form of salts, or elemental sulphur, the fermentation process being stopped at the point at which the proportion of sulphur-containing carbohydrate reaches its maximum, by means of alkalinization of the medium to a pH between 8 and 10 and subjecting the latter to a thermal shock at between 80° and 90° C., the medium finally being acidified or neutralized to a pH between 3 and 6, according to whether a long storage of the liquid concentrate is desired or immediate drying is to be performed.

2. Process claim 1, characterized in that disaccharides, or monosaccharides, or mixtures of polysaccharides obtained by means of hydrolysis of starches, are used as soluble carbohydrates.

3. Process according to claim 1, characterized in that lactic bacteria that produce lactic acid in the L-lactic isomeric form and bacteria of the genus Desulfovibrio, are used.

* * * * *